(12) United States Patent
Nijhof, Jr. et al.

(10) Patent No.: US 11,857,374 B2
(45) Date of Patent: Jan. 2, 2024

(54) REGISTRATION OF X-RAY AND ULTRASOUND IMAGES

(71) Applicant: KONINKLIJKE PHILIPS N.V., Eindhoven (NL)

(72) Inventors: Niels Nijhof, Jr., Utrecht (NL); Godefridus Antonius Harks, Rijen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 642 days.

(21) Appl. No.: 16/631,894

(22) PCT Filed: Jul. 20, 2018

(86) PCT No.: PCT/EP2018/069699
§ 371 (c)(1),
(2) Date: Jan. 17, 2020

(87) PCT Pub. No.: WO2019/020498
PCT Pub. Date: Jan. 31, 2019

(65) Prior Publication Data
US 2020/0155120 A1    May 21, 2020

(30) Foreign Application Priority Data

Jul. 26, 2017  (EP) .................................... 17183317

(51) Int. Cl.
*A61B 8/00* (2006.01)
*A61B 8/08* (2006.01)
(Continued)

(52) U.S. Cl.
CPC .......... *A61B 8/5207* (2013.01); *A61B 6/4417* (2013.01); *A61B 6/5247* (2013.01);
(Continued)

(58) Field of Classification Search
CPC ... A61B 8/5207; A61B 8/0891; A61B 6/4417; A61B 6/5247; A61B 8/0883; A61B 8/12;
(Continued)

(56) References Cited

U.S. PATENT DOCUMENTS 8,126,239 B2    2/2012  Sun
2004/0236220 A1    11/2004  Willis
(Continued)

FOREIGN PATENT DOCUMENTS

| WO | 2008042423 A2 | 4/2008 |
| WO | 2011138698 A1 | 11/2011 |
| WO | 2016033065 A1 | 3/2016 |

OTHER PUBLICATIONS

Mikla et al., "Medical Imaging Technology", 2014 (Year: 2014).*
(Continued)

*Primary Examiner* — Patricia J Park
*Assistant Examiner* — Adil Partap S Virk (57) ABSTRACT

An image registration system (111) for registering a live stream of ultrasound images (112) of a beamforming ultrasound probe (113) with an X-ray image (114) is described. The image registration (111) system identifies, from the X-ray image (114), the position of a medical device (116) represented in the X-ray image (114); and determines, based on ultrasound signals transmitted between the beamforming ultrasound probe (113) and an ultrasound transducer (115) disposed on the medical device (116), a location of the ultrasound transducer (115) respective the beamforming ultrasound probe (113). Each ultrasound image from the live stream (112) is registered with the X-ray (114) image based on the identified position of the medical device (116). The registration includes determining an offset from said identified position that is based on i) a predetermined spatial relationship of the ultrasound transducer (115) respective the
(Continued)

medical device (116) and ii) the determined location of the ultrasound transducer (115) respective the beamforming ultrasound probe (113).

16 Claims, 2 Drawing Sheets

(51) Int. Cl.
 *A61B 6/00* (2006.01)
 *A61B 8/12* (2006.01)
(52) U.S. Cl.
 CPC .............. *A61B 8/0883* (2013.01); *A61B 8/12* (2013.01); *A61B 8/4254* (2013.01); *A61B 8/4416* (2013.01); *A61B 8/5261* (2013.01)
(58) Field of Classification Search
 CPC ... A61B 8/4254; A61B 8/4416; A61B 8/5261; A61B 8/4245; A61B 8/4477
 See application file for complete search history.

(56) References Cited

U.S. PATENT DOCUMENTS

| | | | |
|---|---|---|---|
| 2007/0066968 A1 | 3/2007 | Rahn | |
| 2008/0095421 A1* | 4/2008 | Sun | A61B 6/5247 382/131 |
| 2008/0119727 A1* | 5/2008 | Barbagli | A61B 8/12 600/437 |
| 2008/0262345 A1 | 10/2008 | Fichtinger | |
| 2008/0287783 A1* | 11/2008 | Anderson | A61B 8/5238 600/429 |
| 2010/0063400 A1* | 3/2010 | Hall | A61B 6/4417 378/4 |
| 2010/0239144 A1 | 9/2010 | Fichtinger | |
| 2012/0004529 A1* | 1/2012 | Tolkowsky | A61B 1/0005 600/407 |
| 2012/0245458 A1 | 9/2012 | Gogin | |
| 2013/0245433 A1* | 9/2013 | Deladi | A61B 8/4483 600/424 |
| 2013/0296725 A1* | 11/2013 | Lee | A61B 8/0841 600/509 |
| 2014/0364719 A1* | 12/2014 | Byrd | A61B 5/06 600/409 |
| 2015/0094570 A1* | 4/2015 | Fojtik | A61B 5/0036 606/1 |
| 2015/0250434 A1 | 9/2015 | Hall | |
| 2016/0232655 A1* | 8/2016 | Lachner | G06T 7/344 |
| 2016/0310760 A1 | 10/2016 | Bharat | |
| 2016/0331351 A1 | 11/2016 | Guracar | |

OTHER PUBLICATIONS

International Search Report & Written Opinion of PCT/EP2018/069699, dated Oct. 10, 2018.

Hill, Derek L.G. et al "Medical Image Registration", Physics in Medicine and Biology, vol. 46, R1, R45, 2001.

Lu, Huanxiang et al "A New Sensor Technology for 2D Ultrasound-Guided Needle Tracking", Miccai, Part 11, LNCS 8674, pp. 389, 10 396, 2014.

Kaiser, Markus et al "Significant Acceleration of 2D-3D Registration-based Fusion of Ultrasound and X-ray Images by Mesh-Based DRR Rendering", Proceedings Optical Diagnostics of Living Cells II, vol. 8671, 8676111-1, Medical Imaging 2013: Image-Guided Procedures, Robotic Interventions, and Modeling.

* cited by examiner

REGISTRATION OF X-RAY AND ULTRASOUND IMAGES

CROSS-REFERENCE TO PRIOR APPLICATIONS

This application is the U.S. National Phase application under 35 U.S.C. § 371 of International Application No. PCT/EP2018/069699, filed on Jul. 20, 2018, which claims the benefit of European Patent Application No. 17183317.1, filed on Jul. 26, 2017. These applications are hereby incorporated by reference herein.

FIELD OF THE INVENTION

The invention relates to an image registration system for registering a live stream of ultrasound images of a beamforming ultrasound probe with an X-ray image. The invention may be used in the medical imaging field in general, and more specifically in cardiac or in intra-luminal imaging during an interventional procedure. The invention may be used in medical procedures such as electrophysiology and the treatment of structural heart disease.

BACKGROUND OF THE INVENTION

Interventional procedures are routinely performed under X-ray guidance. X-ray imaging provides good visualization of the medical devices that are used in such procedures but suffers from poor soft tissue contrast. Ultrasound imaging is often used to augment the poor soft tissue contrast of the X-ray images but the visualization of medical devices under ultrasound is often challenging. In particular the specular reflections of the medical devices at certain incidence angles can make it difficult to locate such medical devices in ultrasound images. Known systems that register, or fuse, X-ray images with live ultrasound images provide good soft tissue contrast as well as improved visualization of medical devices.

A document U.S. Pat. No. 8,126,239B2 discloses a method which includes registering a fluoroscopy image with data representing a volume, and identifying a catheter position relative to a volume represented by preoperative volume data. The catheter position is displayed relative to a patient volume represented by data acquired without scanning the catheter.

However there remains room to improve the guidance of interventional devices during medical procedures.

SUMMARY OF THE INVENTION

The present invention seeks to provide an image registration system that mitigates the aforementioned problems. Thereto an image registration system for registering a live stream of ultrasound images of a beamforming ultrasound probe with an X-ray image is provided. The registration is based on i) ultrasound signals transmitted between the beamforming ultrasound probe and an ultrasound transducer that is disposed on a medical device represented in the X-ray image, which ultrasound transducer has a predetermined spatial relationship with the medical device. The registration is also based on ii) a position of the medical device derived from the X-ray image. The image registration system includes at least one processor that is configured to: a) receive the live stream of ultrasound images; b) receive the X-ray image that includes the representation of the medical device; c) identify, from the received X-ray image, a position of the medical device; d) receive transmitted and detected signals corresponding to the ultrasound signals transmitted between the beamforming ultrasound probe and the ultrasound transducer disposed on the medical device; e) determine, based on the received signals, a location of the ultrasound transducer respective the beamforming ultrasound probe by i) selecting an ultrasound beam of the beamforming ultrasound probe corresponding to the maximum detected signal and ii) calculating, for the selected ultrasound beam, a range between the beamforming ultrasound probe and the ultrasound transducer based on a time of flight of said transmitted ultrasound signals; and to f) register each ultrasound image from the live stream with the X-ray image based on the identified position of the medical device, wherein said registration includes determining an offset from said identified position that is based on i) the predetermined spatial relationship of the ultrasound transducer respective the medical device and ii) the determined location of the ultrasound transducer respective the beamforming ultrasound probe.

In so doing the image registration system accurately registers live ultrasound images, i.e. substantially real-time images with high soft tissue contrast, to a corresponding X-ray image. The high tissue contrast provided by the ultrasound images is beneficial for anatomical guidance. The registration is performed using a position of the medical device derived from the X-ray image as a reference position. Any subsequent movement of the beamforming ultrasound probe with respect to the medical device is accounted-for by the registration of the live stream of ultrasound images to the X-ray image. The X-ray image provides good visualization of the medical device and thus the reference position of the medical device is accurately determined. Moreover, the tracking of the medical device using the signals transmitted between the beamforming ultrasound probe and the medical device obviates the need to independently track the beamforming ultrasound probe and the medical device in order to provide the link between the X-ray and ultrasound coordinate systems. The registration accurately aligns the live ultrasound images with the X-ray image because the ultrasound signals, i.e. the ultrasound beams of the beamforming ultrasound probe that are used in the registration, are accurately aligned with respect to the beamforming ultrasound probe. Furthermore, the use of ultrasound signals for the positioning avoids the risk of metallic objects distorting the magnetic fields of known magnetic-based tracking systems. The image registration system can therefore be used to accurately guide a medical device during an interventional procedure. Further advantages from the described invention will also be apparent to the skilled person.

According to one aspect the X-ray image further includes a representation of the ultrasound sensor and/or at least one X-ray fiducial of the medical device. The position of the medical device is identified based further on the position of the ultrasound sensor and/or the at least one X-ray fiducial of the medical device represented in the X-ray image. The position of the ultrasound sensor and/or the at least one X-ray fiducial of the medical device provide additional reference positions in the X-ray image that are used to improve accuracy of the positioning and consequently the accuracy of the registration. These positions may for example improve the determination of the orientation or the rotation of the medical device.

According to another aspect the X-ray image is a historic X-ray image that is generated earlier in time than each ultrasound image of the live stream. In this aspect the at least one processor receives an updated X-ray image that is more recent than the historic X-ray image and replaces the historic X-ray image with the updated X-ray image. The updated X-ray image may consequently indicate recent anatomical changes, or indicate a different position within the anatomy. The latter may be useful when performing medical procedures in a new location in the anatomy.

According to another aspect the live stream of ultrasound images includes a current ultrasound image. In this aspect the image registration system further receives user input indicative of a position in the current ultrasound image, and provides in the registered X-ray image, a marker corresponding to the position in the current ultrasound image. The marker may indicate a position of interest in the anatomy. This may for example be the site of an intended medical procedure such as an ablation. This aspect may therefore be used to improve the guidance of a medical procedure.

According to another aspect the medical device may for example be an esophageal temperature probe. During a medical procedure, an esophageal temperature probe advantageously tends to remain relatively static in the anatomy. Consequently the position of the medical device in the X-ray image remains valid for a long period of time. The live stream of ultrasound images of the beamforming ultrasound probe are therefore accurately registered with the X-ray image for a long period of time after the X-ray image is generated. This reduces the need to make regular X-ray images to reflect the current position of the medical device in the anatomy, and thereby reduces X-ray dose to the patient. Optionally the at least one processor may receive, from the esophageal temperature probe, a temperature signal indicative of a temperature at a position on the esophageal temperature probe and indicate the received temperature at a corresponding position in the registered X-ray image. This may be used to reduce the risk of injury to a patient during a medical procedure.

According to another aspect the X-ray image is a fluoroscopy image; i.e. a live X-ray image. In this aspect a live ultrasound image is therefore registered with a live X-ray image. This aspect offers improved anatomical guidance particularly when the medical device and/or interventional device undergo large or rapid displacements within the anatomy since the most-recent images from each modality are registered.

According to another aspect a computer program product is disclosed. The computer program product includes instructions which when executed on at least one processor of the image registration system; cause the processor to carry out the method steps of: a) receiving the live stream of ultrasound images; b) receiving the X-ray image that includes the representation of the medical device; c) identifying, from the received X-ray image, a position of the medical device; d) receiving transmitted and detected signals corresponding to the ultrasound signals transmitted between the beamforming ultrasound probe and the ultrasound transducer disposed on the medical device; e) determining, based on the received signals, a location of the ultrasound transducer respective the beamforming ultrasound probe by i) selecting an ultrasound beam of the beamforming ultrasound probe corresponding to the maximum detected signal and ii) calculating, for the selected ultrasound beam, a range between the beamforming ultrasound probe and the ultrasound transducer based on a time of flight of said transmitted ultrasound signals; and f) registering each ultrasound image from the live stream with the X-ray image based on the identified position of the medical device, wherein said registration includes determining an offset from said identified position that is based on i) the predetermined spatial relationship of the ultrasound transducer respective the medical device and ii) the determined location of the ultrasound transducer respective the beamforming ultrasound probe.

Further aspects are described with reference to the appended claims.

DETAILED DESCRIPTION OF THE INVENTION

In order to illustrate the principles of the present invention an image registration system for registering a live stream of ultrasound images from an intra cardiac echography, i.e. ICE, beamforming ultrasound probe with an X-ray image is described. It is however to be appreciated that the invention also finds application with beamforming ultrasound probes in general. For example the beamforming ultrasound probe may alternatively be cardiac probe in general, a 2D or a 3D ICE probe, a transesophageal echocardiogram, TEE, probe, a transthoracic echocardiogram, TTE, probe, or an intra vascular ultrasound, IVUS, probe. Moreover, in the described image registration system, reference is made to a static X-ray image. It is also to be appreciated that the invention may also be used with a live stream of X-ray images, i.e. fluoroscopy X-ray images. Moreover an image registration system is described in which the medical device that is represented in the X-ray image is an esophageal temperature probe. Whilst particular reference is made to an esophageal temperature probe it is also to be appreciated that the medical device is not limited to this example and that the medical device may alternatively be for example a catheter, an ablation catheter, a biopsy device, a guidewire, a probe, an endoscope, a robot, a filter device, a balloon device, a stent, a mitral clip, a left atrial appendage closure device, an aortic valve, a pacemaker, an intravenous line, a drainage line, a surgical tool, a tissue sealing device, or a tissue cutting device. The above examples should not be construed as limiting the scope of the invention.

Figure 1:
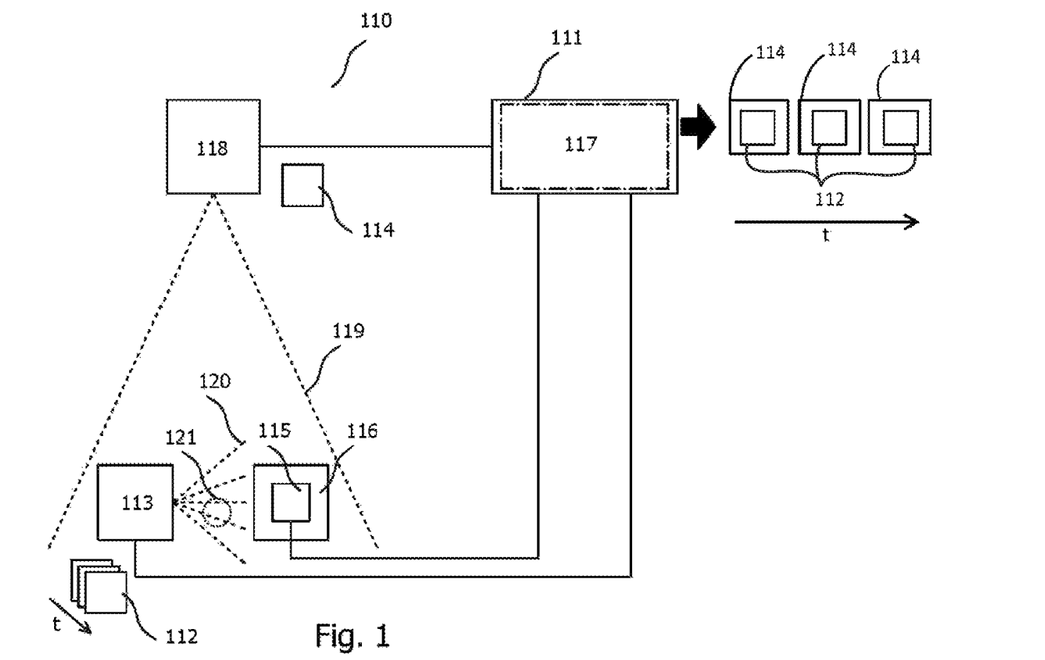
FIG. 1 illustrates an arrangement 110 that includes an image registration system 111 in accordance with some aspects of the invention.

FIG. 1 illustrates an arrangement 110 that includes an image registration system 111 in accordance with some aspects of the invention. Image registration system 111 may be used to register live stream of ultrasound images 112 that are received from beamforming ultrasound probe 113, with X-ray image 114 that is received from X-ray imaging system 118.

Beamforming ultrasound probe 113 in FIG. 1 is an imaging probe that generates a plurality of ultrasound beams that together define its field of view 120. Field of view 120 may include, i.e. overlap with, region of interest 121 which may for example be a portion of the anatomy. In-use, beamforming ultrasound probe 113 may therefore be used to generate an ultrasound image that corresponds to its field of view 120 and which therefore includes region of interest 121. In a specific example, beamforming ultrasound probe 113 may for example be a 2D or a 3D ICE probe that is used to image a region of interest 121 such as a portion of the heart.

During an ultrasound imaging procedure such as brightness-mode, i.e. B-mode, imaging, a one or two-dimensional transducer array within beamforming ultrasound probe 113 transmits a plurality of ultrasound beams of that define its field of view 120. The beams are transmitted in a sequence, or a •frame•. The frame is repeated multiple times in order to generate a live, i.e. substantially real-time, stream of ultrasound images 112. Each beam is generated using known beamforming techniques by applying various delays to the ultrasound signals transmitted by the elements of the transducer array. After each beam is transmitted, beamforming ultrasound probe 113 switches to a receive mode and detects reflected ultrasound signals. One or more associated processors determine the acoustic density along each beam by applying various delays to the ultrasound signals detected by the transducer array. An ultrasound image corresponding to the acoustic density of field of view 120 is determined by the one or more associated processors by combining the responses for all the beams for each frame. The one or more associated processors are not illustrated in FIG. 1, however they may located in beamforming ultrasound probe 113, or in a separate ultrasound console not illustrated in FIG. 1, or alternatively their functionality may be distributed between the one or more processors in beamforming ultrasound probe 113, in the separate ultrasound console, or the one or more processors 117 in image registration system 111.

X-ray imaging system 118 in FIG. 1 has a field of view 119 and may in general be any X-ray imaging system. In one example X-ray imaging system 118 is a C-arm X-ray imaging system, and in another example X-ray imaging system 118 is a computed tomography, i.e. CT, imaging system. X-ray image 114 may therefore be a planar or projection image, or a tomographic image. Moreover, X-ray image may be a fluoroscopic X-ray image, i.e. a live X-ray image.

In-use, X-ray imaging system 118 in FIG. 1 generates X-ray image 114 that includes a representation of medical device 116. Medical device 116 is located within field of view 119 of X-ray imaging system 118 at the time when X-ray image 114 is generated. Consequently at least a portion of medical device 116 is visible in X-ray image 114. Medical device 116 may for example be an esophageal temperature probe. An esophageal temperature probe advantageously remains relatively static during a medical procedure and can therefore provide a relatively fixed reference position. Moreover, medical device 116 in FIG. 1 includes an ultrasound transducer 115. Ultrasound transducer 115 may be an ultrasound emitter or a detector, or indeed be capable of both emitting and detecting ultrasound signals; i.e. a transponder. In-use, ultrasound transducer 115 is within field of view 120 of beamforming ultrasound probe 113 such that either ultrasound transducer 115 is sensitive to at least one of the ultrasound beams transmitted by beamforming ultrasound probe 113, or such that beamforming ultrasound probe 113 is sensitive, within at least one of its ultrasound beams, to ultrasound signals emitted by ultrasound transducer 115. In a preferred configuration ultrasound transducer 115 is a detector that is sensitive to the ultrasound signals emitted by beamforming ultrasound probe 113.

Moreover, ultrasound transducer 115 disposed on medical device 116 has a predetermined spatial relationship with medical device 116. In one example ultrasound transducer 115 may be arranged at a known position or orientation or rotation with respect to a position on medical device 116. In one example medical device 116 may include a distal end and ultrasound transducer 115 may be arranged at a known distance from the distal end. In another example medical device 116 may include a body having an axis, and ultrasound transducer 115 may be arranged at a known rotational angle with respect to the axis of the body. In another example multiple ultrasound transducers 115 may be disposed on medical device 116. The multiple ultrasound transducers may for example be arranged in a known pattern with respect to e.g. the distal end of medical device 116.

Various types of ultrasound transducer are contemplated for use as ultrasound transducer 115 in FIG. 1. These include piezoelectric, piezoresistive and capacitive transducers. More specifically, micro electro mechanical system, i.e. MEMS, or capacitive micro-machined ultrasound transducers, i.e. CMUT-type ultrasound transducers may also be used. Suitable piezoelectric materials include polymer piezoelectric materials such as Polyvinylidene fluoride, a PVDF co-polymer such as polyvinylidene fluoride trifluoroethylene, or a PVDF ter-polymer such as P(VDF-TrFE-CTFE). Polymer piezoelectric materials offer high flexibility and thus may be conformally attached to surfaces having non-flat topography. Preferably a non-imaging ultrasound transducer is used, i.e. an ultrasound transducer that has inadequate pixels or is otherwise not controlled so as to generate an image, however it is also contemplated that an imaging transducer may be used. In other words, ultrasound transducer 115 may form part of an imaging array of an imaging medical device 116.

In FIG. 1, connections between image registration system 111 and X-ray imaging system 118, ultrasound transducer 115, and beamforming ultrasound probe 113 are illustrated as being wired connections. The wired connections facilitate the reception or transmission of data such as signals, and/or control signals between the various units. It is also contemplated to replace one or more of these wired connections with wireless connections. Moreover, X-ray image 114 may be received from a memory rather than, as illustrated, being received directly from X-ray imaging system 118.

As mentioned above, image registration system 111 in FIG. 1 includes at least one processor 117. The at least one processor 117 is configured to a) receive live stream of ultrasound images 112 b) receive X-ray image 114 that includes the representation of medical device 116 c) identify, from received X-ray image 114, a position of medical device 116 d) receive transmitted and detected signals corresponding to the ultrasound signals transmitted between beamforming ultrasound probe 113 and ultrasound transducer 115 disposed on medical device 116 e) determine, based on the received signals, a location of ultrasound transducer 115 respective beamforming ultrasound probe 113 by i) selecting an ultrasound beam of beamforming ultrasound probe 113 corresponding to the maximum detected signal and ii) calculating, for the selected ultrasound beam, a range between beamforming ultrasound probe 113 and ultrasound transducer 115 based on a time of flight of said transmitted ultrasound signals; and to f) register each ultrasound image from live stream 112 with X-ray image 114 based on the identified position of medical device 116. The registration includes determining an offset from said identified position that is based on i) the predetermined spatial relationship of ultrasound transducer 115 respective medical device 116 and ii) the determined location of ultrasound transducer 115 respective beamforming ultrasound probe 113.

Consequently, the registration of live stream of ultrasound images 112 with X-ray image 114 in step f) is determined using two offsets from the position of medical device 116 in X-ray image 114. The first offset is defined by the known spatial relationship between ultrasound transducer 115 and medical device 116. The second offset is defined by the location of ultrasound transducer 115 with respect to beamforming ultrasound probe 113. Depending on the actual positions, the offset may be for example a translation, a rotation or a combination of a rotation and a translation. Many suitable techniques for performing such rotations and translations in the registration are known from the medical image registration field. Known registration techniques from the medical imaging field such as those described in the document: Medical image registration, Hill, D. L. G, et al, PHYSICS IN MEDICINE AND BIOLOGY, Phys. Med. Biol. 46 (2001) R1, R45, may be used. In particular, rigid body transformations that incorporate offsets i) and ii), may be used in the registration.

In respect of step c) above, i.e. identifying, from received X-ray image 114, a position of the medical device 116, various methods are contemplated. In a preferred implementation a representation of the medical device is registered with the X-ray image using known medical image registration techniques. One suitable technique is implemented in the Philips Echonavigator system. This involves adjusting the position of a model of the medical device in two- or three-dimensional image space until its position best matches that in the X-ray image. The matching position may for example be determined using a least squares or minimum energy calculation. The image registration may for example compute gradients in the X-ray image and/or apply an edge-detection algorithm to the X-ray image in order to determine an outline of medical device 116. Suitable known edge detection methods include frequency domain filtering and Fourier transformations.

In respect of steps d) and e) above, i.e. determining a location of ultrasound transducer 115 respective beamforming ultrasound probe 113 based on ultrasound signals transmitted between the beamforming ultrasound probe 113 and the ultrasound transducer 115 disposed on the medical device; a technique may be implemented that is similar to that described in document WO 2011/138698A1 and in the publication •A New Sensor Technology for 2D Ultrasound-Guided Needle Tracking•, Huanxiang Lu et al, MICCAI 2014, Part II, LNCS 8674, pp. 389, 10 396, 2014.

With reference to FIG. 1, in this technique, ultrasound transducer 115 is preferably a detector that is sensitive to the imaging ultrasound signals that are emitted by beamforming ultrasound probe 113. As described above, in a conventional ultrasound imaging mode, for example a brightness, i.e. B-mode, the one or two-dimensional transducer array of beamforming ultrasound probe 113 transmits a sequence of beams within its field of view 120 in order to generate each ultrasound image. Each beam is generated by applying various delays to the ultrasound signals transmitted by the elements of the transducer array. After each beam is transmitted, beamforming ultrasound probe 113 switches to a receive mode and determines the acoustic density along the beam by applying various delays to the ultrasound signals detected by the transducer array. An ultrasound image corresponding to the acoustic density of field of view 120 is determined by combining the responses for all the beams for each frame. When ultrasound transducer 115 is within field of view 120 of beamforming ultrasound probe 113, each emitted ultrasound beam will be detected with a signal strength that depends in part on its lateral displacement from that beam. The closest beam to detector 115 generates the maximum detected signal strength, and this beam identifies the angle or bearing between beamforming ultrasound probe 113 and ultrasound transducer 115. The actual beam in which detector 115 is located is determined by image registration system 111 using knowledge of the timing of the transmission of the beam within each imaging frame. Furthermore, the range between beamforming ultrasound probe 113 and ultrasound transducer 115 is calculated by image registration system 111 from the time of flight of that beam, i.e. the time between its transmission by the transducer array of beamforming ultrasound probe 113 and its detection by ultrasound transducer 115. Since the angle and range between beamforming ultrasound probe 113 and ultrasound transducer 115 is known, this provides the location of the ultrasound transducer 115 respective beamforming ultrasound probe 113. This technique may be used in a similar manner with other ultrasound imaging modes.

In one variation of the above technique, instead of using the ultrasound imaging beams of beamforming ultrasound probe 113 to determine the relative position of ultrasound transducer 115, dedicated tracking beams may likewise be transmitted and detected in the same manner to determine the relative position of ultrasound transducer 115. These tracking beams may be interleaved temporally between the imaging beams; for example they may be transmitted within an image frame or between image frames. Advantageously these tracking beams do not necessarily have to spatially coincide with, or have the same spatial resolution as the imaging beams. In another variation of the above technique, instead of ultrasound transducer 115 being a detector, an ultrasound emitter may be used. In this variation the ultrasound emitter may periodically emit an ultrasound pulse or signature that, following a correction for the time of emission of the pulse, appears in the live stream of ultrasound images generated by beamforming ultrasound probe 113 as a bright spot at the position of ultrasound emitter 115. In another variation of the above technique ultrasound transducer 115 may operate as a transponder that issues an ultrasound pulse or signature upon detection of an ultrasound signal from beamforming ultrasound probe 113. Again, following a correction for the time of emission of the pulse, the position of emitter 115 appears in the live stream of ultrasound images as a bright spot. Thus, in each of these described variations, a location of ultrasound transducer 115 respective the beamforming ultrasound probe 113 is determined based on ultrasound signals transmitted between beamforming ultrasound probe 113 and an ultrasound transducer 115 disposed on a medical device 116.

Moreover the location of ultrasound transducer 115 respective beamforming ultrasound probe 113 is determined in step e) by i) selecting an ultrasound beam of the beamforming ultrasound probe corresponding to the maximum detected signal and ii) calculating, for the selected ultrasound beam, a range between the beamforming ultrasound probe and the ultrasound transducer based on a time of flight of said transmitted ultrasound signals. It is noted that when ultrasound transducer 115 operates as an emitter, steps i) and ii) are inherently performed by the processor of the beamforming ultrasound probe when it provides the position of the emitter as a bright spot in the live stream of ultrasound images.

Finally, in respect of step f), each ultrasound image from live stream 112 is registered with X-ray image 114 based on the identified position of medical device 116. The registration includes determining an offset from said identified position that is based on i) the predetermined spatial relationship of ultrasound transducer 115 respective medical device 116 and ii) the determined location of ultrasound transducer 115 respective the beamforming ultrasound probe 113.

In one implementation X-ray image 114 includes an X-ray image coordinate system and live stream of ultrasound images 112 includes an ultrasound image coordinate system that is fixed with respect to the beamforming ultrasound probe 113. The at least one processor 117 may be configured register each ultrasound image from the live stream 112 with the X-ray image 114 based on the identified position of medical device 116 by mapping the ultrasound image coordinate system to the X-ray image coordinate system. The ultrasound image coordinate system, and/or the X-ray image coordinate system may for example be a polar, a Cartesian coordinate system, a cylindrical or a spherical coordinate system. Various mapping techniques are contemplated for this and are well known from the medical image registration field.

In one implementation the at least one processor 117 of image registration system 111 in FIG. 1 is configured to display each ultrasound image of the live stream 112 consecutively as an overlay on the X-ray image 114. In other words a fused image comprising the current or most-recent ultrasound image of the live stream 112 may be displayed.

Figure 2:
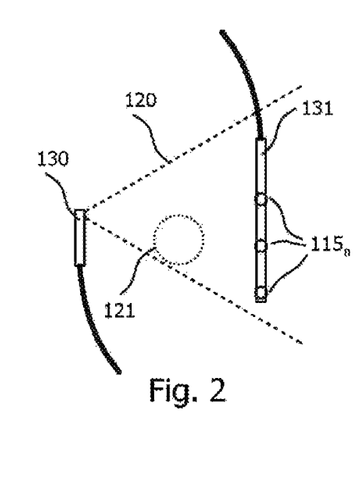
FIG. 2 illustrates a first embodiment of an ICE catheter 130 with an esophageal temperature probe 131 within its field of view 120.

In order to improve the accuracy of the registration performed in step f), the accuracy of determining the location of ultrasound transducer 115 in step e) may optionally be improved by including one or more additional ultrasound transducers on medical device 116. Thereto, FIG. 2 illustrates a first embodiment of an ICE catheter 130 with an esophageal temperature probe 131 within its field of view 120. ICE catheter 130 corresponds to beamforming ultrasound probe 113 in FIG. 1 and esophageal temperature probe 131 corresponds to medical device 116 in FIG. 1. In FIG. 2, ICE catheter 130 has field of view 120 that includes, i.e. overlaps with region of interest 121. ICE catheter 130 is therefore arranged to generate a live stream of images 112 that includes region of interest 121. Esophageal temperature probe 131 is included in, i.e. overlapped by, field of view 121. Multiple ultrasound transducers 115$_n$ are disposed on esophageal temperature probe 131 and configured to detect ultrasound beams transmitted by ICE catheter 130. The locations of each of the multiple ultrasound transducers 115$_n$ are determined respective ICE catheter 130 in the same manner as described above for the single ultrasound transducer in FIG. 1. The additional location information provided by multiple ultrasound transducers 115$_n$ improves the accuracy of determining the location of esophageal temperature probe 131 respective ICE catheter 130. For example, the multiple ultrasound transducers 115$_n$ provide redundancy such that if one of the transducer is outside field of view 120, one of the others may be within the field of view. Moreover, the multiple positions ultrasound transducers 115$_n$ provide additional rotation and/or orientation information about medical device 116 that may result in a more accurate registration in step f).

Figure 3:
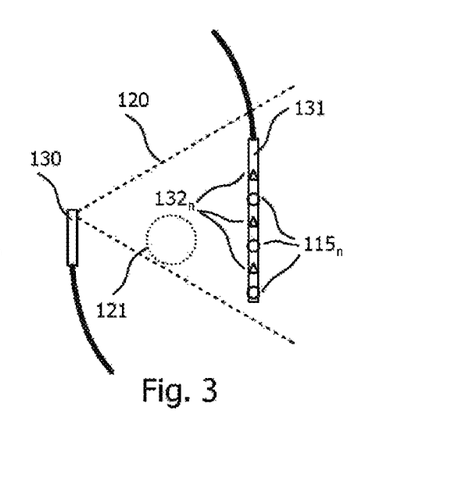
FIG. 3 illustrates a second embodiment of an ICE catheter 130 with an esophageal temperature probe 131 within its field of view 120.

In order to even further improve the accuracy of the registration performed in step f) above, the identification of the position of medical device 116 in X-ray image 114 in step c) may optionally be improved. Thereto the position of the ultrasound sensor, as identified in the X-ray image, may be used to provide an additional reference point on medical device 116 to improve the identification of the position of medical device 116. An outline of the ultrasound sensor may for example be represented in the X-ray image owing to its characteristic shape or its characteristic X-ray absorption. Alternatively, one or more X-ray fiducials may be included on medical device 116. These fiducials are consequently represented in X-ray image 114 and may be used in the same manner to identify the position of medical device 116 in X-ray image 114. Thereto, FIG. 3 illustrates a second embodiment of an ICE catheter 130 with an esophageal temperature probe 131 within its field of view 120. Esophageal temperature probe 131 in FIG. 3 includes multiple X-ray fiducials 132$_n$. An X-ray fiducial has a characteristic X-ray Hounsfield unit absorption that allows it to be identified as such in the X-ray image, thereby allowing its distinction from typical anatomical image features such as tissue and bone. Clearly, multiple X-ray fiducials 132$_n$ may be alternatively used in combination with a single ultrasound transducer 115. Preferably, X-ray fiducials 132$_n$ and/or ultrasound transducers 115$_n$ are arranged in a known configuration, or pattern, respective esophageal temperature probe 131 in order to simplify their identification and consequently this known pattern is used in identifying the position of esophageal temperature probe 131 in X-ray image 114. Again, a model that includes the known pattern in relation to esophageal temperature probe 131 may be used as described above in relation to medical device 116 to determine the position of esophageal temperature probe 131.

In one embodiment, X-ray image 114 in FIG. 1 is a historic X-ray image that is generated earlier in time than each ultrasound image of live stream 112. In this embodiment, the at least one processor 117 receives an updated X-ray image that is more recent than the historic X-ray image and replaces the historic X-ray image with the updated X-ray image. The most recent X-ray image may thereby indicate recent anatomical changes, or indicate a different position within the anatomy. The latter may be useful when performing medical procedures in a new location in the anatomy.

In another embodiment, live stream of ultrasound images 112 in FIG. 1 includes a current ultrasound image, i.e. a most recent, or a substantially real-time, ultrasound image. In this embodiment image registration system 111 is arranged to receive user input indicative of a position in the current ultrasound image, and provides in the registered X-ray image, a marker corresponding to the position in the current ultrasound image. User input may be received from user input device such as a switch, a keyboard, a mouse or a joystick. User input may for example be received from a switch or other control associated with beamforming ultrasound probe 113 or associated with medical device 116. A user may for example move a mouse cursor to a position in the current ultrasound image, click the mouse, and this position be indicated in the current ultrasound image by the marker. Various shapes and/or colors may be used for the marker, such as a circle or a cross and so forth. The marker may be displayed for a predetermined period of time, or indefinitely thereafter, to act as a record. In one example the user input is received from beamforming ultrasound probe 113. The marker may for example indicate a position at which a subsequent medical procedure is planned to take place. A surgeon may for example use this facility as a navigational aid, e.g. to mark a ventricle in the heart, or as a reminder to return to that position later during a medical procedure to ablate tissue. In another example, medical device 116 in FIG. 1 is an esophageal temperature probe and the at least one processor 117 receives, from the esophageal temperature probe, a temperature signal indicative of a temperature at a position on the esophageal temperature probe. Moreover the at least one processor 117 is configured to indicate at a corresponding position in the registered X-ray image 114, the received temperature. In so doing the registered, or fused image that is generated by image registration system 111 may display a record of the temperature that was recorded at the designated position. The temperature may be a historic or a live, i.e. substantially real-time, temperature. The temperature may thereby serve as a warning to a surgeon of the risk of damaging healthy tissue during a cardiac ablation procedure. User input may alternatively be received from a separate interventional device not illustrated in FIG. 1 such as a cardiac ablation catheter. In one example user input is received from a cardiac ablation catheter and corresponds to the activation of the catheter. The marker that is provided in the registered or fused X-ray image corresponds to the position of the activation and serves as an indication to an operator of each ablation point in the anatomy. In summary, the marker may therefore indicate a position of interest in the anatomy.

Figure 4:
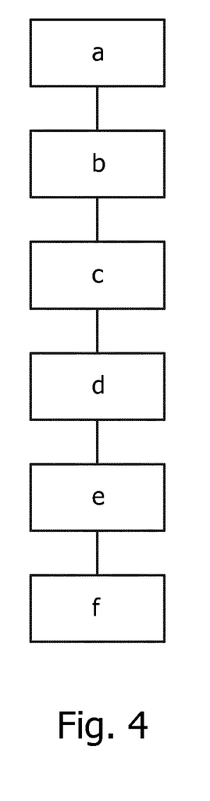
FIG. 4 illustrates various method steps that may be carried out by the computer program product.

In another embodiment a computer program product is disclosed for use with image registration system 111 in FIG. 1. Thereto, FIG. 4 illustrates various method steps that may be carried out by the computer program product. The computer program product includes instructions which when executed on at least one processor 117 of image registration system 111; cause processor(s) 117 to carry out the method steps of: a) receiving live stream of ultrasound images 112; b) receiving X-ray image 114 that includes the representation of medical device 116; c) identifying, from received X-ray image 114, a position of medical device 116; d) receiving transmitted and detected signals corresponding to the ultrasound signals transmitted between beamforming ultrasound probe 113 and ultrasound transducer 115 disposed on medical device 116; e) determining, based on the received signals, a location of ultrasound transducer 115 respective beamforming ultrasound probe 113 by i) selecting an ultrasound beam of beamforming ultrasound probe 113 corresponding to the maximum detected signal and ii) calculating, for the selected ultrasound beam, a range between beamforming ultrasound probe 113 and ultrasound transducer 115 based on a time of flight of said transmitted ultrasound signals; and f) registering each ultrasound image from live stream 112 with X-ray image 114 based on the identified position of medical device 116, wherein said registration includes determining an offset from said identified position that is based on i) the predetermined spatial relationship of ultrasound transducer 115 respective medical device 116 and ii) the determined location of ultrasound transducer 115 respective beamforming ultrasound probe 113. The computer program product may further include instructions to perform additional method steps described herein in relation to image registration system 111.

The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term •processor• or •controller• should not be construed to refer exclusively to hardware capable of executing software, and can implicitly include, without limitation, digital signal processor •DSP• hardware, read only memory •ROM• for storing software, random access memory •RAM•, non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory •RAM•, a read-only memory •ROM•, a rigid magnetic disk and an optical disk. Current examples of optical disks include compact disk, read only memory •CD-ROM•, compact disk, read/write •CD-R/W•, Blu-Rayf and DVD.

In summary, an image registration system for registering a live stream of ultrasound images of a beamforming ultrasound probe with an X-ray image has been described. The image registration system identifies, from the X-ray image, the position of a medical device represented in the X-ray image; and determines, based on ultrasound signals transmitted between the beamforming ultrasound probe and an ultrasound transducer disposed on the medical device, a location of the ultrasound transducer respective the beamforming ultrasound probe. Each ultrasound image from the live stream is registered with the X-ray image based on the identified position of the medical device. The registration includes determining an offset from said identified position that is based on i) a predetermined spatial relationship of the ultrasound transducer respective the medical device and ii) the determined location of the ultrasound transducer respective the beamforming ultrasound probe. Various embodiments and options have been described in relation the system, and it is noted that the various embodiments may be combined to achieve further advantageous effects.

The invention claimed is:

1. A system, comprising:
at least one processor configured for communication with:
   a beamforming ultrasound probe; and
   a medical device comprising a distal end, an axis, and an ultrasound transducer with a predetermined spatial relationship with respect to the medical device, wherein the predetermined spatial relationship comprises a position of the ultrasound transducer relative to the distal end or an orientation of the ultrasound transducer relative to the axis, wherein the at least one processor is configured to:
control the beamforming ultrasound probe to obtain a live stream of ultrasound images of an anatomy of a patient, wherein the live stream of ultrasound images includes a current ultrasound image;
control the beamforming ultrasound probe to transmit an ultrasound signal;
determine a location of the ultrasound transducer relative to the beamforming ultrasound probe based on the ultrasound transducer receiving the ultrasound signal;
receive an x-ray image of the anatomy that depicts the medical device;
identify a position of the medical device in the x-ray image;
perform registration of each ultrasound image from the live stream with the X-ray image based on the position of the medical device;
receive, via the current ultrasound image, an input indicative of a site of an interventional procedure in the anatomy; and provide, based on the registration, a marker in the registered x-ray image that identifies the site of the interventional procedure in the registered x-ray image,
wherein, to perform the registration, the at least one processor is configured to determine, for each ultrasound image, an offset from the position of the medical device in the x-ray image, wherein the offset is based on:
the predetermined spatial relationship of the ultrasound transducer with respect to the medical device; and
the location of the ultrasound transducer relative to the beamforming ultrasound probe.

2. The system according to claim 1,
wherein the X-ray image further includes a representation of the ultrasound transducer, and
wherein the at least one processor is configured to identify, from the received X-ray image, the position of the medical device based further on a position of the ultrasound transducer represented in the X-ray image.

3. The system according to claim 1,
wherein the medical device further includes at least one X-ray fiducial that is represented in the X-ray image, and
wherein the at least one processor is configured to identify, from the received X-ray image, the position of the medical device based further on a position of the at least one X-ray fiducial represented in the X-ray image.

4. The system according to claim 1, wherein the at least one processor is configured to identify, from the received X-ray image, the position of the medical device by registering a representation of the medical device with the X-ray image.

5. The system according to claim 1, wherein the at least one processor is further configured to display each ultrasound image of the live stream consecutively as an overlay on the X-ray image.

6. The system according to claim 1,
wherein the X-ray image is a historic X-ray image that is generated earlier in time than each ultrasound image of the live stream, and
wherein the at least one processor is further configured to receive an updated X-ray image that is more recent than the historic X-ray image and to replace the historic X-ray image with the updated X-ray image.

7. The system according to claim 1, wherein the ultrasound transducer is a non-imaging ultrasound transducer.

8. The system according to claim 7,
wherein the live stream of ultrasound images includes a current ultrasound image, and
wherein the at least one processor is further configured to:
receive user input indicative of a position in the current ultrasound image; and
provide in the X-ray image a marker corresponding to the position in the current ultrasound image.

9. The system according to claim 7, wherein the medical device is an esophageal temperature probe.

10. The system according to claim 9, wherein the at least one processor is further configured to:
receive, from the esophageal temperature probe, a temperature signal indicative of a temperature at a position on the esophageal temperature probe; and
indicate at a corresponding position in the X-ray image, the received temperature.

11. The system according to claim 10,
wherein the X-ray image includes an X-ray image coordinate system and the live stream of ultrasound images includes an ultrasound image coordinate system that is fixed with respect to the beamforming ultrasound probe; and
wherein the at least one processor is configured register each ultrasound image from the live stream with the X-ray image based on the identified position of the medical device by mapping the ultrasound image coordinate system to the X-ray image coordinate system.

12. The system according to claim 1, wherein the beamforming ultrasound probe comprises at least one of:
i) a cardiac probe;
ii) an intra cardiac echoscopy (ICE) probe;
iii) a transesophageal echocardiogram (TEE) probe;
iv) a transthoracic echocardiogram (TTE) probe; or
iv) an intra vascular ultrasound (IVUS) probe.

13. The system according to claim 1, wherein the X-ray image is a fluoroscopy image.

14. The system according to claim 1, further comprising at least one of: an X-ray imaging system for providing the X-ray image, a beamforming ultrasound probe, a medical device, the ultrasound transducer of the medical device, or at least one X-ray fiducial for providing a corresponding fiducial representation in the X-ray image.

15. The system of claim 1, wherein, to determine the location of the ultrasound transducer, the at least one processor is configured to calculate a range between the beamforming ultrasound probe and the ultrasound transducer based on a time of flight of the ultrasound signal.

16. A non-transitory computer readable medium having stored thereon a plurality of instructions executable by at least one processor configured for communication with a beamforming ultrasound probe and a medical device comprising a distal end, an axis, and an ultrasound transducer with a predetermined spatial relationship with respect to the medical device, wherein the predetermined spatial relationship comprises a position of the ultrasound transducer relative to the distal end or an orientation of the ultrasound transducer relative to the axis, wherein, when executed, the plurality of instructions cause the at least one processor to:
control the beamforming ultrasound probe to obtain a live stream of ultrasound images of an anatomy of a patient, wherein the live stream of ultrasound images includes a current ultrasound image;
control the beamforming ultrasound probe to transmit an ultrasound signal;
determine a location of the ultrasound transducer relative to the beamforming ultrasound probe based on the ultrasound transducer receiving the ultrasound signal;
receive an x-ray image of the anatomy that depicts the medical device;
identify a position of the medical device in the x-ray image;
perform registration of each ultrasound image from the live stream with the X-ray image based on the position of the medical device;
receive, via the current ultrasound image, an input indicative of a site of an interventional procedure in the anatomy; and
provide, based on the registration, a marker in the registered x-ray image that identifies the site of the interventional procedure in the registered x-ray image,
wherein, to perform the registration, the plurality of instructions cause the at least one processor is configured to determine, for each ultrasound image, an offset from the position of the medical device in the x-ray image, wherein the offset is based on:

the predetermined spatial relationship of the ultrasound transducer with respect to the medical device; and the location of the ultrasound transducer relative to the beamforming ultrasound probe.

* * * * *